(12) United States Patent
Hasnah et al.

(10) Patent No.: US 7,076,025 B2
(45) Date of Patent: Jul. 11, 2006

(54) METHOD FOR DETECTING A MASS DENSITY IMAGE OF AN OBJECT

(75) Inventors: Moumen O. Hasnah, Doha (QA); Leroy Dean Chapman, Saskatoon (CA)

(73) Assignee: Illinois Institute of Technology, Chicago, IL (US)

(*) Notice: Subject to any disclaimer, the term of this patent is extended or adjusted under 35 U.S.C. 154(b) by 0 days.

(21) Appl. No.: 10/848,969

(22) Filed: May 19, 2004

(65) Prior Publication Data

US 2005/0259788 A1 Nov. 24, 2005

(51) Int. Cl.
*G01T 1/36* (2006.01)
(52) U.S. Cl. ............................................. 378/82; 378/84
(58) Field of Classification Search ................. 378/70, 378/71, 80, 82, 83, 84, 87, 89, 73
See application file for complete search history.

(56) References Cited

U.S. PATENT DOCUMENTS

| | | |
|---|---|---|
| 2,543,630 A | 2/1951 | Hansen |
| 2,853,617 A | 9/1958 | Berreman |
| 3,032,656 A | 5/1962 | Hosemann et al. |
| 3,439,163 A | 4/1969 | DeJongh |
| 3,628,040 A | 12/1971 | Schnopper et al. |
| 3,777,156 A | 12/1973 | Hammond et al. |
| 3,885,153 A | 5/1975 | Schoenborn et al. |
| 4,223,219 A | 9/1980 | Born et al. |
| 4,351,063 A | 9/1982 | Dineen et al. |
| 4,599,741 A | 7/1986 | Wittry |
| 4,625,323 A | 11/1986 | Okaya |
| 4,649,557 A | 3/1987 | Hornstra et al. |
| 4,737,973 A | 4/1988 | Ogawa et al. |
| 4,949,367 A | 8/1990 | Huizing et al. |
| 5,123,036 A | 6/1992 | Uno et al. |
| 5,127,028 A | 6/1992 | Wittry |
| 5,164,975 A | 11/1992 | Steinmeyer |
| 5,195,115 A | 3/1993 | Schiller et al. |

(Continued)

FOREIGN PATENT DOCUMENTS

WO 95/05725 2/1995

OTHER PUBLICATIONS

D. Chapman, W. Thomlinson, R.E. Johnson, D. Washburn, E. Pisano. N. Gmür, Z. Zhong, R. Menk, F. Arfelli and D. Sayers, *X-Ray Refraction Imaging (XRI) Applied to Mammography*, published Oct. 31, 1997.

(Continued)

*Primary Examiner*—David V. Bruce
*Assistant Examiner*—Hoon Song
(74) *Attorney, Agent, or Firm*—Pauley Peterson & Erickson

(57) ABSTRACT

A method for detecting a mass density image of an object. An x-ray beam is transmitted through the object and a transmitted beam is emitted from the object. The transmitted beam is directed at an angle of incidence upon a crystal analyzer. A diffracted beam is emitted from the crystal analyzer onto a detector and digitized. A first image of the object is detected from the diffracted beam emitted from the crystal analyzer when positioned at a first angular position. A second image of the object is detected from the diffracted beam emitted from the crystal analyzer when positioned at a second angular position. The first image and the second image are combined mathematically to derive a mass density image of the object.

20 Claims, 3 Drawing Sheets

U.S. PATENT DOCUMENTS

| | | | |
|---|---|---|---|
| 5,245,648 | A | 9/1993 | Kinney et al. |
| 5,259,013 | A | 11/1993 | Kuriyama et al. |
| 5,319,694 | A | 6/1994 | Ingal et al. |
| 5,406,609 | A | 4/1995 | Arai et al. |
| 5,428,657 | A | 6/1995 | Papanicolopoulos et al. |
| 5,457,726 | A | 10/1995 | Miyazaki |
| 5,457,727 | A | 10/1995 | Frijlink |
| 5,579,363 | A | 11/1996 | Ingal et al. |
| 5,715,291 | A | 2/1998 | Momose |
| 5,717,733 | A | 2/1998 | Kurbatov et al. |
| 5,787,146 | A | 7/1998 | Giebeler |
| 5,802,137 | A | 9/1998 | Wilkins |
| 5,805,662 | A | 9/1998 | Kurbatov et al. |
| 5,850,425 | A | 12/1998 | Wilkins |
| 5,923,720 | A | 7/1999 | Barton et al. |
| 5,949,847 | A | 9/1999 | Terada et al. |
| 5,987,095 | A * | 11/1999 | Chapman et al. ............. 378/70 |
| 6,035,227 | A | 3/2000 | Shmueli |
| 6,038,285 | A | 3/2000 | Zhong et al. |
| 6,269,144 | B1 | 7/2001 | Dube et al. |
| 6,385,289 | B1 | 5/2002 | Kikuchi |
| 6,567,496 | B1 * | 5/2003 | Sychev ........................ 378/57 |
| 6,577,708 | B1 | 6/2003 | Chapman et al. |
| 6,804,324 | B1 | 10/2004 | Martynov et al. |
| 6,870,896 | B1 * | 3/2005 | Protopopov ................... 378/36 |
| 2002/0136352 | A1 | 9/2002 | Protopopov |
| 2004/0196957 | A1 | 10/2004 | Ando |

OTHER PUBLICATIONS

V.N. Ingal and E.A. Beliaevskaya, *Phase Dispersion Introscopy*, (published prior to Oct. 16, 1996).

V.N. Ingal and E.A. Beliaevskaya, *X-ray plane-wave topography observation of the phase contrast from a non-crystalline object*, J. Phys. D: Appl. Phys. 28 (1995) 2314-2317.

V.N. Ingal and E.A. Belyaevskaya, *Method of phase-dispersion introscopy*, Tech. Phys. 42 (1), Jan. 1997.

V.N. Ingal and E.A. Beliaevskaya, *Phase dispersion radiography of biological objects*, Physica Medica. vol. X11, No. 2, Apr.-Jun. 1996.

V.A. Bushuev, V.N. Ingal and E.A. Belyaevskaya, *Dynamical Theory of Images Generated by Noncrystalline Objects for the Method of Phase-Dispersive Introscopy*, Crystallography Reports, vol. 41, No. 5, 1996, pp. 766-774.

V.A. Bushuev, E.A. Beliaevskaya and V.N. Ingal, *Wave-optical description of X-ray phase contrast images of weakly absorbing non-crystalline objects*, II Nuovo Cimento, vol. 19D, No. 2-4, Feb.-Apr. 1997.

V.N. Ingal and E.A. Beliaevskaya, *Imaging of biological objects in the plane-wave diffraction scheme*, II Nuovo Cimento, vol. 19D, No. 2-4, Feb.-Apr. 1997.

V.N. Ingal and E.A. Beliaevskaya, *Phase Dispersion Introscopy, Surface Investigation*, vol. 12, pp. 441-450, 1997.

Tetsuya Ishikawa, Selshi Kikuta and Kazutaka Kohra, *Angle-Resolved Plane Wave X-Ray Topography*, Japanese Journal of Applied Physics, vol. 24, No. 7, Jul. 1985, pp. L559-L562.

R.C. Blasdell and A.T. Macrander, *Prototype grooved and spherically bent Si backscattering crystal analyzer for meV resolution inelastic x-ray scattering*, Review of Scientific Instruments, vol. 66, No. 2, Feb. 1995, pp. 2075-2077, New York.

*Monochromatic energy-subtraction radiography using a rotating anode source and a bent Laue monochromator*, a paper published in Phys. Med. Biol., 42 (1997), pp. 1751-1762.

*A bent Laue crystal monochromator for monochromatic radiography with an area beam*, a paper published in Nuclear Instruments and Methods in Physics Research, Section A, 399 (1997), pp. 489-498.

Kenneth Lange et al.: *EM Reconstruction Algorithms for Emission and Transmission Tomography*, Journal of Computer Assisted Tomography, pp. 306-316, 1984.

A.P. Dempster et al.: *Maximum Likelihood from Incomplete Data via the EM Algorithm*, pp. 1-38, 1976.

Hasnah et al.: *Diffraction Enhanced Imaging Contrast Mechanisms in Breast Cancer Specimens*, Medical Physics 29, pp. 2216-2221, 2002.

J.L. Cronin in *Modern dispenser cathodes*, IEE Proc., vol. 128, Pt. 1, No. 1, (Feb. 1981).

* cited by examiner

METHOD FOR DETECTING A MASS DENSITY IMAGE OF AN OBJECT

This work was supported in part by U.S. Army Medical Research and Material Command grant DAMD 17-99-1-9217 and State of Illinois Higher Education Cooperative Agreement.

FIELD OF THE INVENTION

This invention relates to a method for detecting an image of an object, such as one mass internal with respect to another mass wherein the one mass has an absorption content, refraction content, and/or density content different from the other mass. The method of this invention measures the intensity of an x-ray beam as it emits from an object, preferably as a function of angle, and derives a mass density image from the measured intensity.

BACKGROUND OF THE INVENTION

X-ray imaging has been used in the medical field and for radiology in general, such as non-destructive testing and x-ray computed tomography. Conventional radiography systems use x-ray absorption to distinguish differences between different materials, such as normal and abnormal human tissues.

Conventional x-ray radiography measures the projected x-ray attenuation, or absorption, of an object. Attenuation differences within the object provide contrast of embedded features that can be displayed as an image. For example, cancerous tissues generally appear in conventional radiography because these tissues are more dense than the surrounding non-cancerous tissues. The best absorption contrast is generally obtained at x-ray energies where the absorption is high. Conventional radiography is typically performed using lower x-ray energy in higher doses to allow greater absorption and, thus, better contrast and images. Using x-rays having higher energy generally requires a lower dosage to be used because of patient safety concerns. In general, as the x-ray energy level increases and the x-ray dose used decreases, the quality of the conventional radiography image lessens.

Diffraction Enhanced Imaging (DEI), for example, as disclosed in U.S. Pat. No. 5,987,095, issued to Chapman et al., and U.S. Pat. No. 6,577,708, issued to Chapman et al., is a radiographic technique that derives contrast from an object's x-ray absorption, refraction and ultra-small-angle scattering properties. DEI can be used to detect, analyze, combine and visualize the refraction, absorption and scattering effects upon an image of an object. DEI is particularly useful for relatively thick and thus highly absorbing materials. Compared to the absorption contrast of conventional radiography, the additional contrast mechanisms, refraction and scatter, of DEI allow visualization of more features of the object.

DEI, and the method of this invention, can use highly collimated x-rays prepared by x-ray diffraction from perfect single-crystal silicon. These collimated x-rays are of single x-ray energy, practically monochromatic, and are used as the beam to image an object. A schematic of a DEI setup is shown in FIG. 1. In this case, the collimated x-rays are prepared by two silicon (3, 3, 3) crystals of a monochromator 11. Once this beam passes through the object, another crystal of the same orientation and using the same reflection is introduced. This crystal is called an analyzer 30. If this crystal is rotated about an axis perpendicular to the plane shown in FIG. 1, the crystal will rotate through a Bragg condition for diffraction and the diffracted intensity will trace out a profile that is called a rocking curve, such as shown in FIG. 2. The profile will be roughly triangular and will have peak intensity close to that of the beam intensity striking the analyzer crystal. The width of the profile is typically a few microradians wide, for example 3.6 microradians within a full width of half maximum (FWHM) at 18 keV using the silicon (3, 3, 3) reflection. The character of the images obtained change depending on the setting of the analyzer crystal. To extract refraction information, the analyzer is typically set to the half intensity points on low ($R_L$) and high ($R_H$) angle sides of the rocking curve. At least two images are obtained by a detector at different angled positions, for example, one at each of the low and high angle sides of the rocking curve, of the crystal analyzer. The images are mathematically combined to obtain images, such as a refraction angle image.

DEI can use higher x-ray energy levels than generally available for obtaining absorption images using conventional radiography. One advantage of using higher x-ray energies is a lower dose is required. A second advantage is that higher x-ray energies reduce the flux required of an imaging system, as the transmission through the object is high. However, applying DEI at higher x-ray energy levels with a lower dose can lead to the loss of a good absorption-based radiograph, as x-ray absorption is lower at higher energy levels. Therefore, acceptance of DEI by radiologists may be limited without the ability to create an image resembling a conventional radiograph.

There is a need for an imaging method that provides an image having characteristics similar to a conventional radiograph at higher x-ray energy levels and lower doses, such as used in DEI. There is a need for an imaging method that provides an image having characteristics similar to a conventional radiograph, and where the image is a property of the object with no direct dependence on the imaging x-ray energy level.

SUMMARY OF THE INVENTION

It is one object of this invention to provide a method for detecting an image of an object and using the image to determine differences in the composition of matter and/or structural arrangement of the object.

It is another object of this invention to provide a method for detecting an image having the contrast features of conventional radiography and using relatively high x-ray energy levels at relatively low doses, as compared to conventional radiography.

It is yet another object of this invention to provide a method for detecting an image of an object by deriving contrast from differences in mass density within the object.

The above and other objects of this invention are accomplished with a method that irradiates an x-ray beam, such as a mono-energetic beam, through an object and directs a transmitted beam, which is emitted from the object, at an angle of incidence upon a crystal analyzer, such as a Bragg type crystal analyzer or a Laue type crystal analyzer. A diffracted beam emitted from the crystal analyzer is used to detect an intensity image of the object. Intensity images are detected at least at two positions of the crystal analyzer, and then the images are mathematically combined to derive a mass density image of the object. The method of this invention provides a clear image of the object that does not directly depend on the energy level of the x-ray beams.

The imaging method according to this invention uses an image processing algorithm on digitized images obtained, for example, by Diffraction Enhanced Imaging (DEI). Once the images of the object are digitized, a relatively simple algorithm can be used to independently determine the mass density image. The method according to this invention works with either a Laue type crystal analyzer, which is a transmission type analyzer, or a Bragg type crystal analyzer, which is a reflection type analyzer.

The method according to this invention does not depend upon phase contrast due to x-ray absorption, as in conventional radiography, to determine the image of an object. Rather, the mass density image provided by the method according to this invention is obtained by an algorithm that reduces DEI refraction images into mass density images. Thus, the mass density image is a property of the object and does not directly depend on the energy level of the imaging x-ray beams. The mass density image of this invention can also be obtained with lower x-ray doses than conventional radiography generally allows. In one embodiment according to this invention, the mass density image can be obtained with a reduction in x-ray doses by at least a factor of 10, and even greater than a factor of 40, compared to conventional radiography used for mammography, and with better signal to noise ratios.

BRIEF DESCRIPTION OF THE DRAWINGS

The above-mentioned and other features and objects of this invention will be better understood from the following detailed description of preferred embodiments taken in conjunction with the drawings.

FIG. 4A shows a radiograph of the breast cancer specimen at an x-ray energy level of 18 keV. FIG. 4B shows a DEI refraction image of the breast cancer specimen at an x-ray energy level of 40 keV. FIG. 4C shows a radiograph of the breast cancer specimen at an x-ray energy level of 40 keV. FIG. 4D shows a mass density image obtained by processing the 40 keV refraction image shown in FIG. 4B.

DESCRIPTION OF PRESENTLY PREFERRED EMBODIMENTS

One method of this invention provides a mass density image of an object. The mass density image shows contrast features of an object, similar to conventional radiography, without relying on the absorption of x-rays by the object. The mass density image of an object is obtained through an image processing algorithm used on images based on refraction characteristics of the object, such as refraction images obtained by Diffraction Enhanced Imaging (DEI). The mass density image of this invention can be obtained through DEI such as, for example, the x-ray imaging method disclosed in U.S. Pat. No. 5,987,095 issued to Chapman et al. and/or in U.S. Pat. No. 6,577,708 issued to Chapman et al., the entire disclosures of which are incorporated into this specification by reference.

Figure 1:
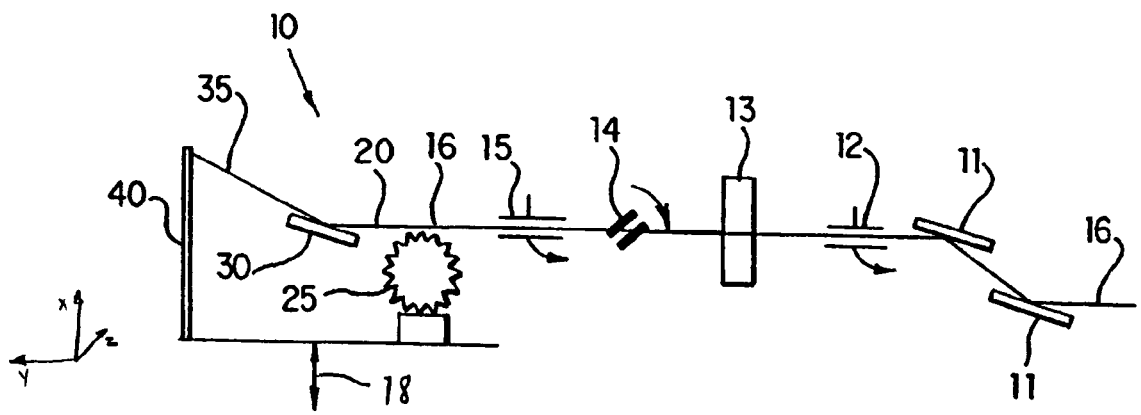
FIG. 1 is a schematic diagram of a crystal analyzer system including a Bragg type crystal analyzer, according to one preferred embodiment of this invention.

FIG. 1 shows a schematic diagram of an analyzer system 10, according to one preferred embodiment of this invention. FIG. 1 is similar to the crystal analyzer system shown in FIG. 1 of U.S. Pat. No. 5,987,095 issued to Chapman et al. A crystal analyzer 30, as shown in FIG. 1, represents a Bragg type crystal analyzer. It is apparent that a Laue type analyzer or other similar type analyzer can also be used to produce the same result of generating a diffracted beam 35, for analysis purposes.

The double crystal monochromator 11 can be used to generate an x-ray beam 16, such as a monochromatic x-ray beam. Each crystal of the monochromator 11 is preferably constructed of silicon using a (3, 3, 3) lattice planes structure. The lattice planes used in the monochromator 11, such as the (3, 3, 3) lattice planes, should preferably match those used in the crystal analyzer 30. Through experimentation, the (3, 3, 3) lattice planes structure increased the sensitivity to refraction effects by a factor of about 5, when compared to experiments conducted with (1, 1, 1) lattice planes structure. As will be appreciated by one skilled in the art following the teachings provided in this specification and in the claims, sources of monochromatic x-ray beams other than the monochromator 11 can be used to generate a monochromatic x-ray beam 16.

The mass density image is a property of the object and does not directly depend on the imaging energy. The mass density image can be derived from an imaging system, such as a DEI system, that can derive refraction angle contrast. DEI systems can typically derive refraction images using any x-ray energy level, including energy levels of approximately 40 keV or higher. According to one preferred embodiment of this invention, an x-ray beam 16 has an energy level in a range of approximately 16 keV to approximately 100 keV, more desirably approximately 18 keV to approximately 40 keV, with a bandwidth of approximately 1.5 keV. In one preferred embodiment according to this invention, the x-ray beam 16 is approximately 80 mm wide and approximately 0.1 mm high. A shutter 14, such as a rotary shutter or the like, can be used to control exposure and limit unnecessary scatter.

Any suitable detector known to those skilled in the art can be used to detect an image of an object 25. In one preferred embodiment according to this invention, the object 25 image is detected with an image plate which comprises a photo-stimulable phosphor image plate typically used for radiology, such as FUJI Medical Systems high resolution HR5 and standard resolution ST5 image plates. An image recorded on an image plate 40 can be digitized, stored and displayed, for example by a FUJI Medical Systems AC3 reader and workstation or by any other suitable digital convertor known to those skilled in the art. One suitable spatial resolution of images can be 0.1×0.1 mm$^2$.

According to one preferred embodiment of this invention, the object 25 and the image plate 40 or another suitable detector can be scanned together, such as in a direction shown by the vertical arrow 18 in FIG. 1, to provide a two-dimensional image of the object 25 taken in the x-z plane, where the z-direction is perpendicular to the plane shown in FIG. 1. Such scanning can be accomplished, for example by a computer controlled stepper motor translation stage which holds a support for the object 25 and which also holds an image plate cassette.

An ionization chamber 12 can be used downstream of the monochromator 11, for example to monitor tuning. The ionization chamber 15, as shown in FIG. 1, which is positioned upstream of the object 25, can be used to monitor a radiation dose at a surface of the object 25.

The crystal analyzer 30 is preferably positioned between the object 25 and the image plate 40. The crystal analyzer 30 is preferably fixed spatially with respect to the transmitted beam 20, oriented to diffract the transmitted beam 20 onto the image plate 40. Fine angular control of the crystal analyzer 30 can be accomplished with a stepper motor driven translation stage pushing on a relatively long rod which is mechanically connected to an axle onto which the crystal analyzer 30 is attached, or with any other suitable mechanical or electromechanical system that has fine angular control. The fine angular control may result in a resolution limit of approximately 1 microradian. Such fine tuning can position crystal analyzer 30 at various positions within the rocking curve of the crystal analyzer 30.

Figure 2:
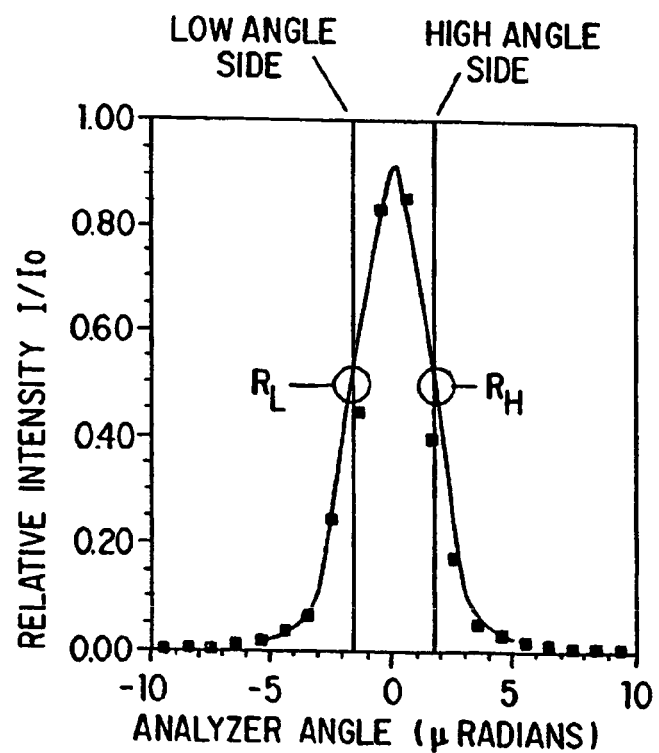
FIG. 2 shows a graphical representation of an analyzer rocking curve for a silicon Bragg type crystal analyzer having (3, 3, 3) lattice planes at an x-ray energy level of approximately 18 keV.

The crystal analyzer 30 can be used to detect the x-ray refraction angles within the transmitted beam 16 as the crystal analyzer 30 has a relatively steep intensity versus angle dependence. The intensity as a function of a crystal angle curve is called the rocking curve or the reflectivity curve. The sensitivity function of analyzer system 10, or the rocking curve of analyzer system 10, characterizes the x-ray output as a function of the angular position of analyzer system 10 when no object is present in the transmitted beam 16, as prepared by the monochromator 11. As shown in FIG. 2, the solid line curve represents a theoretical calculation of the rocking curve for crystal analyzer 30. The square points along the rocking curve represent measured points taken during an experiment conducted according to the method disclosed in U.S. Pat. No. 5,987,095.

In one preferred embodiment according to this invention, two images of the object 25 are detected with the image plate 40. A first image of the object 25 is detected and digitized from the diffracted beam 35 emitted from the crystal analyzer 30 at a first angular position. A second image of the object 25 is detected and digitized from the diffracted beam 35 emitted from the crystal analyzer 30 at a second angular position. In one embodiment according to this invention, the first and second angular positions are on opposing sides of the rocking curve of the crystal analyzer 30. For example, the first angular position of the crystal analyzer 30 can be at a low angle setting of the rocking curve of the crystal analyzer 30 and the second angular position of the crystal analyzer 30 can be at a high angle setting of the rocking curve of the crystal analyzer 30. The first and second images are mathematically combined to derive a mass density image of the object 25.

In one embodiment according to this invention, the first and second images are digitized and combined to derive a refraction image, and the mass density image is derived from the refraction image. The refraction image, like an absorption image obtained by conventional radiography, depends on contrast, or the density change, between two materials of object 25, such as a body embedded within a matrix material. However, the refraction image is a measure of the gradient of the projected density of the object 25. The refraction angle image depends on the spatial gradient of the thickness of the embedded object whereas a conventional absorption image depends only on the thickness.

Conventional radiography derives image contrast from spatial variations, such as due to an embedded object within a matrix material, in the projected absorption of the object being imaged. If two regions are compared in an image, the contrast is:

$$C(x_i, z_j) \cong (\mu_2 - \mu_1) t_2(x_i, z_j) \qquad \text{Equation 1}$$

In Equation 1, $\mu_1$ is the linear attenuation coefficient of the matrix material, $\mu_2$ is the linear attenuation coefficient of the embedded object, and $t_2$ is the thickness of the embedded object. Referring to FIG. 1, the first and second images of the object 25 are obtained by intensity measurements taken at each pixel $(x_i, z_j)$ in the x-z plane. The spatial coordinates and indices of Equation 1 refer to the pixel location within the image, and are designated to be consistent with FIG. 1. In some instances, especially for soft tissue imaging, the absorption contrast results from a density change within the object. Therefore, Equation 1 can be modified as:

$$C(x_i, z_j) \cong \frac{\bar{\mu}}{\rho}(\rho_2 - \rho_1) t_2(x_i, z_j) \qquad \text{Equation 2}$$

where $\rho_1$ is the mass density of the matrix material, $\rho_2$ is the mass density of the embedded object, and $\bar{\mu}/\rho$ is the average mass attenuation for the materials.

In DEI, two images are obtained of the object from which a refraction image can be derived. The refraction image is a measure of the gradient of the projected density of the object and can be expressed as:

$$\theta(x_i, z_j) = K(\rho_2 - \rho_1) \frac{\partial t_2(x_i, z_j)}{\partial z} \qquad \text{Equation 3}$$

where $\rho_1$ and $\rho_2$ are the mass densities of the matrix material and the embedded object, respectively, $\partial t_2/\partial z$ is the thickness gradient of the embedded material in the direction perpendicular to the x-ray beam direction and lying in the diffraction plane, and $$K = \frac{1 r_e \lambda^2}{4\pi u},$$

where $r_e$ is the classical electron radius ($2.82 \times 10^{-15}$ meters), $\lambda$ is the x-ray wavelength, and u is the unified atomic mass unit ($1.66 \times 10^{-27}$ kilograms).

It has been discovered that an integral in the gradient direction of the refraction image of Equation 3 results in an image proportional to the density and thickness of the object in Equation 2. As the refraction image is a pixilated image, the integral is converted to the following summation which is used to construct the mass density image of this invention:

$$(\rho_2 - \rho_1) t_2(x_i, z_j) = \sum_{k=o}^{j} \frac{z_p}{K} \theta(x_i, z_j) \qquad \text{Equation 4}$$

where $z_p$ is the pixel size in the z-direction.

In one embodiment of this invention, a material having a known density is preferably imaged along with the object 25 at either or both z extremes of the image field. The mass density image is the result of a summation that is best applied when the edge of the image field region extends beyond the object so that the mass density does not have offsets.

Figure 3A:
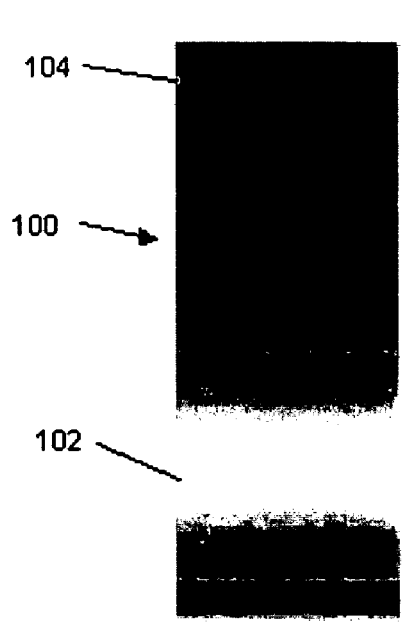
FIG. 3A shows a photograph of a test object imaged by conventional radiography and the method according to this invention.

FIG. 3A shows a diagram of a test object 100 including two solid Lucite rods immersed in water. Lucite has a density of 1.19 g/cm$^3$. The test object was imaged at two x-ray energy levels, 18 keV and 40 keV, by a conventional radiography method and DEI. The 18 keV energy level is approximately the energy level commonly used in mammography by conventional radiography. The 40 keV energy level is an estimated optimal energy for DEI. The large rod 102 had a diameter of 6.35 mm and the small rod 104 had a diameter of 1.0 mm. During the imaging processes, the object 100 was oriented such that the DEI sensitive direction (the z-direction) and the direction of the transmitted x-ray beam was perpendicular to the longitudinal axis of the rods 102 and 104.

Figure 3B:
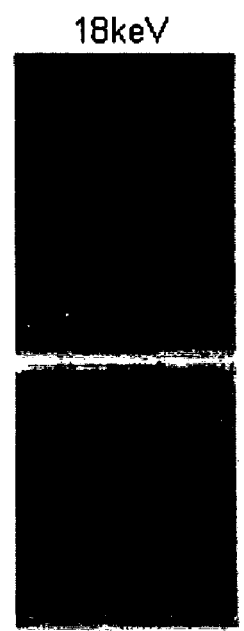
FIG. 3B shows a DEI refraction image of the object shown in FIG. 3A at an x-ray energy level of 18 keV.
Figure 3C:
FIG. 3C shows a radiograph of the object shown in FIG. 3A at an x-ray energy level of 18 keV.
Figure 3D:
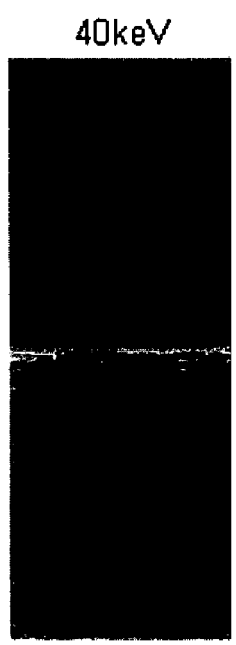
FIG. 3D shows a DEI refraction image of the object shown in FIG. 3A at an x-ray energy level of 40 keV.
Figure 3E:
FIG. 3E shows a radiograph of the object shown in FIG. 3A at an x-ray energy level of 40 keV.
Figure 3F:
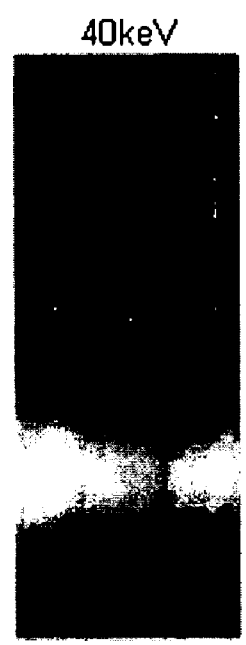
FIG. 3F shows a mass density image of the object shown in FIG. 3A at an x-ray energy level of 40 keV.

FIG. 3B shows a DEI refraction image of the object 100 at an 18 keV energy level. For comparison, FIG. 3C shows a radiograph image of the object 100 at an 18 keV energy level. The images of FIGS. 3B and 3C were taken at an exposure of approximately 7 mGy. FIG. 3D is the DEI refraction image of the object 100 taken at a 40 keV energy level. FIG. 3E is the radiograph image of the object 100 at a 40 keV energy level. FIG. 3F is the mass density ($\Delta\rho t$) image. The exposure for the 40 keV radiograph was 0.12 mGy and the exposure for the refraction image was 0.24 mGy.

The mass density image of FIG. 3F was prepared by summing pixels vertically from the bottom to the top using Equation 4 with the constraint that the $\Delta\rho t$ at the top line of the image is zero. The thickness and density of each of the rods 102 and 104 are known. The $\Delta\rho t$ at the thickest region of the rod 102 is 0.12 g/cm$^2$ as $\Delta\rho t=(\rho_{Lucite}-\rho_{Water})t_{Lucite}$, and $(1.19 \text{ g/cm}^3 - 1.00 \text{ g/cm}^3)0.635 \text{ cm} = 0.12 \text{ g/cm}^2$. The 40 keV mass density image gave a measured value of 0.15±0.02 g/cm$^2$. The 40 keV radiograph had a measured value of zero.

Figure 4A:
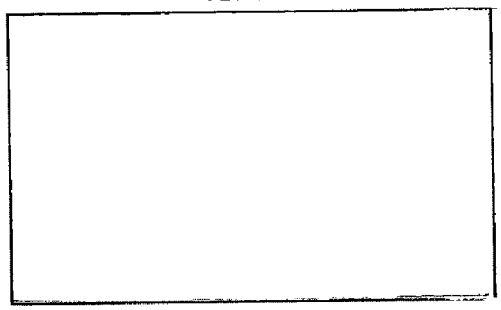
FIGS. 4A through 4D show images of a breast cancer specimen.
Figure 4B:
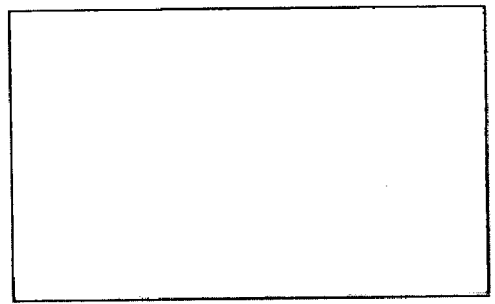
Figure 4C:
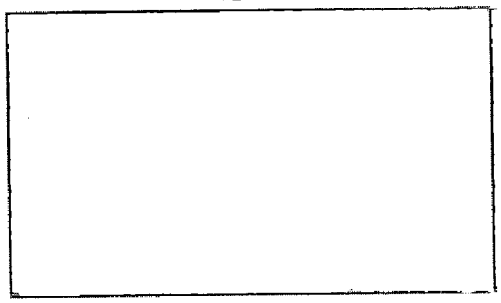
Figure 4D:
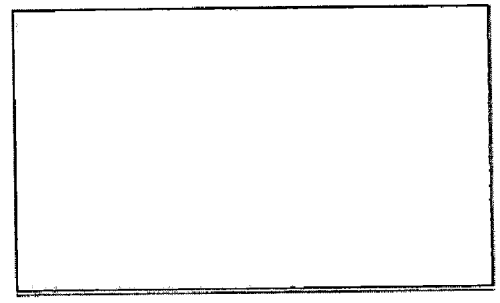

FIGS. 4A–D are images of a breast cancer specimen imaged in the same manner as the test object 100. The breast cancer specimen was a mastectomy specimen approximately 2 cm thick with infiltrating ductal carcinoma. The sample was fixed in formalin and immobilized by threads and Lucite plates to avoid movement during the imaging processes. FIG. 4A shows a radiograph image of the sample at an 18 keV energy level with exposure of approximately 7 mGy. FIG. 4B shows a DEI refraction image of the sample at a 40 keV energy level with exposure of approximately 0.40 mGy. FIG. 4C shows a radiograph image of the sample at 40 keV and translated into a $\Delta\rho t$ image. FIG. 4C indicates that there is little absorption information available by conventional radiography at higher energy levels. FIG. 4D is the mass density ($\Delta\rho t$) image obtained by processing the 40 keV refraction image of FIG. 4B. The mass density image shows characteristics of the sample similar to the radiograph at 18 keV. However, the denser cancerous tissue is visualized by the radiograph by the absorption of the tissues and the mass density image directly visualizes the same property without relying on absorption.

A DEI refraction image can thus be used to obtain a mass density image with properties similar to an absorption image obtained by conventional radiography. The mass density image is a property of the object, and the mass density image does not directly depend on the imaging energy level. The only energy dependence arises from the ability of the DEI system to derive a refraction image contrast. As the refraction sensitivity of the DEI imaging system can be changed, the imaging system can be modified to obtain the level of mass density contrast sensitivity required for a specific application. This modification can be accomplished by using other diffraction planes or crystal in the DEI analyzer system. In addition, the mass density image can have contrast that exceeds the contrast of a conventional radiograph.

While the embodiments of this invention as described are presently preferred, various modifications and improvements can be made without departing from the spirit and scope of this invention. The scope of this invention is indicated by the appended claims, and all changes that fall within the meaning and range of equivalents are intended to be embraced within the appended claims.

What is claimed is:

1. A method for detecting an image of an object, comprising:
   transmitting an x-ray beam through the object and emitting from the object a transmitted beam;
   directing the transmitted beam at an angle of incidence upon a crystal analyzer;
   detecting a first image of the object from a first diffracted beam emitted from the crystal analyzer positioned at a first angular position;
   detecting a second image of the object from a second diffracted beam emitted from the crystal analyzer positioned at a second angular position;
   combining the first image and the second image to derive a refraction image; and
   deriving a mass density image of the object from the refraction image.

2. The method of claim 1, further comprising:
   detecting the first image of the object from the first diffracted beam emitted from the crystal analyzer at a low rocking curve angle setting of the crystal analyzer, and
   detecting the second image of the object from the second diffracted beam emitted from the crystal analyzer at a high rocking curve angle setting of the crystal analyzer.

3. The method of claim 1, wherein the first image and the second image are exposed on a detector capable of producing a digitized image.

4. The method of claim 3, wherein the exposed first image and the exposed second image are digitized.

5. The method of claim 4, wherein the digitized images are mathematically combined to form a digitized refraction image.

6. The method of claim 5, wherein the refraction image and the mass density image are defined on a pixel-by-pixel basis.

7. The method of claim 1, wherein the crystal analyzer is one of a Laue crystal analyzer and a Bragg crystal analyzer.

8. The method of claim 1, wherein the x-ray beam has an energy level of at least about 16 keV.

9. The method of claim 1, wherein the x-ray beam has an energy level of at least about 40 kev.

10. The method according to claim 1 wherein the x-ray beam has an energy level in a range of approximately 16 keV to approximately 100 keV.

11. In a method according to claim 1 wherein the x-ray beam is diffracted by a monochromator which is matched in orientation and lattice planes to the crystal analyzer.

12. In a method according to claim 1 further comprising increasing a relative intensity of the image of the object by adjusting an angular position of the crystal analyzer.

13. In a method according to claim 12 wherein the angular position of the crystal analyzer is adjusted in steps of approximately 1 microradian increments.

14. The method of claim 1, wherein the x-ray beam is monochromatic.

15. The method of claim 1, wherein deriving a mass density image of the object from the refraction image comprises using an algorithm including:

$$(\rho_2 - \rho_1)t_2(x_i, z_j) = \sum_{k=o}^{j} \frac{z_p}{K} \theta(x_i, z_j).$$

where $\rho_1$ is the mass density of the matrix material, $\rho_2$ is the mass density of the embedded object, $t_2$ is the thickness of the embedded object, $(x_i, z_j)$ represents a pixel in the x-z direction, and $z_p$ is the pixel size in the z-direction.

16. A method for detecting an image of an object, comprising:
   transmitting an x-ray beam through the object and emitting from the object a transmitted beam;
   directing the transmitted beam at an angle of incidence upon a crystal analyzer;
   detecting a first image of the object from a first diffracted beam emitted from the crystal analyzer positioned at a first angular position;
   detecting a second image of the object from a second diffracted beam emitted from the crystal analyzer positioned at a second angular position;
   combining the first image and the second image to derive a refraction image; and
   converting the refraction image to a mass density image of the object according to an algorithm comprising:

$$(\rho_2 - \rho_1)t_2(x_i, z_j) = \sum_{k=o}^{j} \frac{z_p}{K} \theta(x_i, z_j).$$

where $\rho_1$ is the mass density of the matrix material, $\rho_2$ is the mass density of the embedded object, $t_2$ is the thickness of the embedded object $(x_i, z_j)$ represents a pixel in the x-z direction, and $z_p$ is the pixel size in the z-direction.

17. The method of claim 16, further comprising:
   detecting the first image of the object from the first diffracted beam emitted from the crystal analyzer at a low rocking curve angle setting of the crystal analyzer; and
   detecting the second image of the object from the second diffracted beam emitted from the crystal analyzer at a high rocking curve angle setting of the crystal analyzer.

18. The method of claim 16, wherein the first image and the second image each comprise a digitized image.

19. The method of claim 18, wherein the first and second images are mathematically combined to form a digitized refraction image.

20. The method of claim 19, wherein the refraction image and the mass density image are defined on a pixel-by-pixel basis.

* * * * *